United States Patent
Kreuzer

(10) Patent No.: US 6,349,436 B1
(45) Date of Patent: Feb. 26, 2002

(54) OPERATING APPARATUS COMPRISING AN OPERATING SUPPORT POST WITH A DETACHABLE OPERATING TABLE TOP

(75) Inventor: Friedhelm Kreuzer, München (DE)

(73) Assignee: Kreuzer GmbH & Co. OHG, Puchheim (DE)

( * ) Notice: Subject to any disclaimer, the term of this patent is extended or adjusted under 35 U.S.C. 154(b) by 0 days.

(21) Appl. No.: 09/514,755

(22) Filed: Feb. 28, 2000

(30) Foreign Application Priority Data

Mar. 9, 1999 (DE) .......................... 199 10 289

(51) Int. Cl.$^7$ .............................................. A61G 13/02
(52) U.S. Cl. .................................. 5/600; 5/83.1; 5/85.1
(58) Field of Search ...................... 5/81.1 R, 81.1 HS, 5/83.1, 85.1, 600

(56) References Cited

U.S. PATENT DOCUMENTS

| | | | |
|---|---|---|---|
| 3,757,420 A | * 9/1973 | Silverman | 32/22 |
| 4,011,609 A | * 3/1977 | Bethlen | 5/600 |
| 5,475,884 A | * 12/1995 | Kirmse et al. | 5/600 |
| 5,477,570 A | * 12/1995 | Hannant et al. | 5/600 |
| 5,490,293 A | * 2/1996 | Nilsson | 5/83.1 |
| 5,735,278 A | 4/1998 | Hoult et al. | |
| 5,842,987 A | * 12/1998 | Sahadevan | 600/407 |
| 6,006,377 A | * 12/1999 | Asakawa | 5/83.1 |
| 6,170,102 B1 | * 1/2001 | Kreuzer | 5/600 |

FOREIGN PATENT DOCUMENTS

| | | |
|---|---|---|
| DE | 196 25 407 A1 | 1/1998 |
| DE | 297 20 449 U1 | 6/1998 |
| EP | 0 215 212 | 3/1987 |
| EP | 1034768 A1 * | 2/2000 |

* cited by examiner

*Primary Examiner*—Michael F. Trettel
(74) *Attorney, Agent, or Firm*—George W. Neuner, Esq.; Dike, Bronstein, Roberts & Cushman, IP Group of Edwards & Angell, LLP

(57) ABSTRACT

An operating apparatus comprises an operating table with an operating support post, an operating table top and means for detachably fastening said operating table top to said operating support post, an anesthesis station and an examining station located at a distance from said operating support post and comprising an examining support post for receiving said operating table top. An overhead rail extends above said operating table and said examining station, and an overhead conveyor comprising means for carrying said operating table top is mounted on said overhead rail for movement therealong from a first position above said operating support post to a second position above said examining station. An overhead support carrying said anesthesis station is also mounted on said overhead rail for movement therealong. First coupling means are provided on said overhead conveyor and second coupling means are provided on said overhead support. The first coupling means engages the second coupling means in the first position of the overhead conveyor.

11 Claims, 3 Drawing Sheets receiving/depositing position

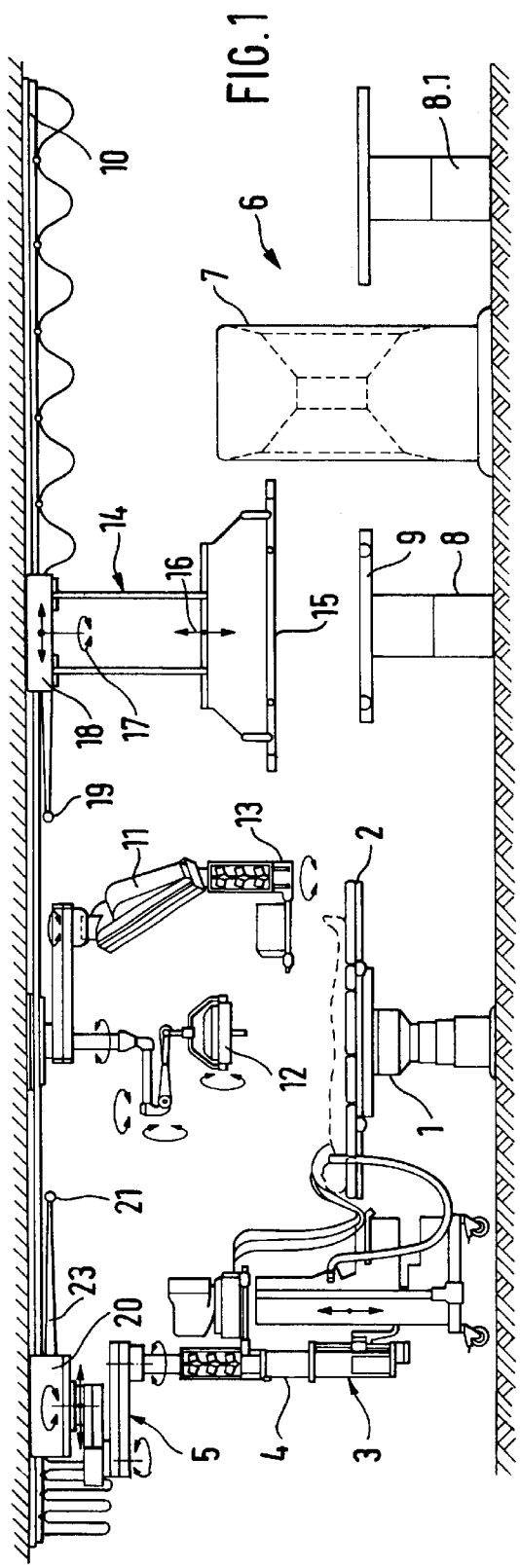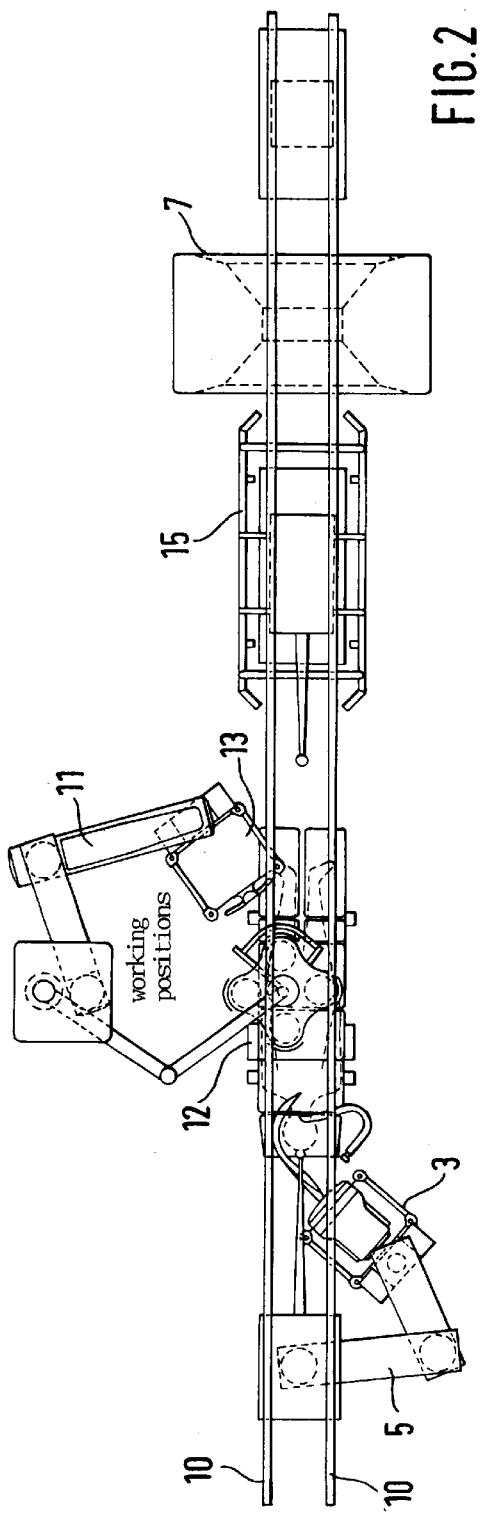

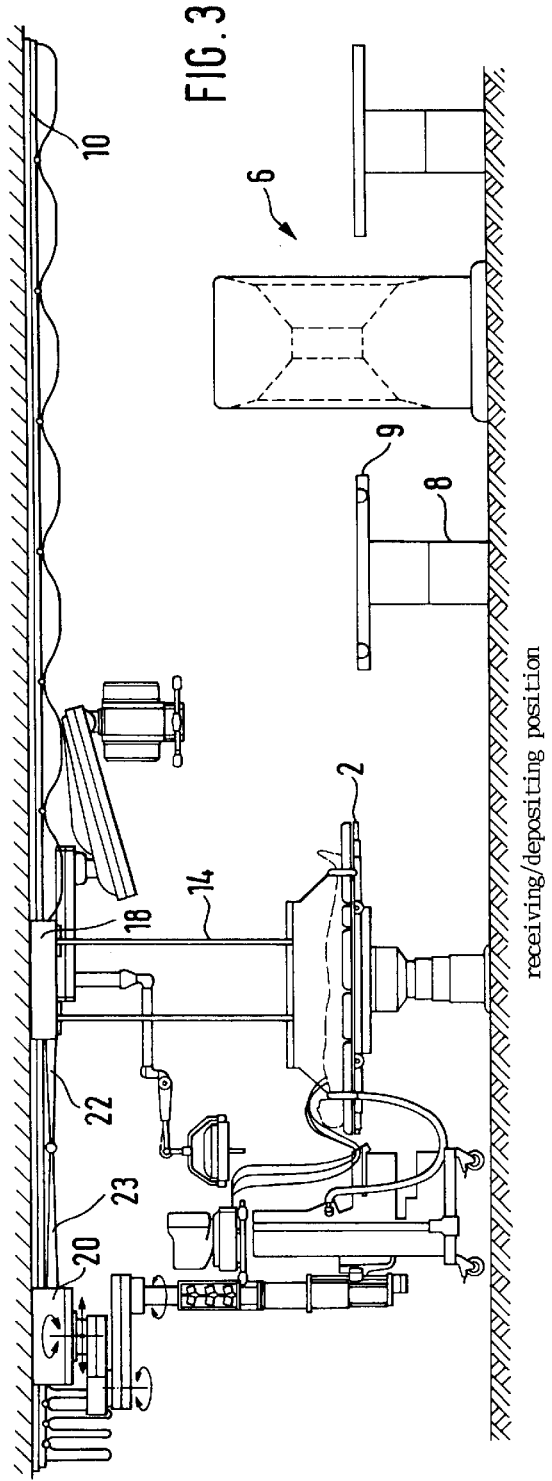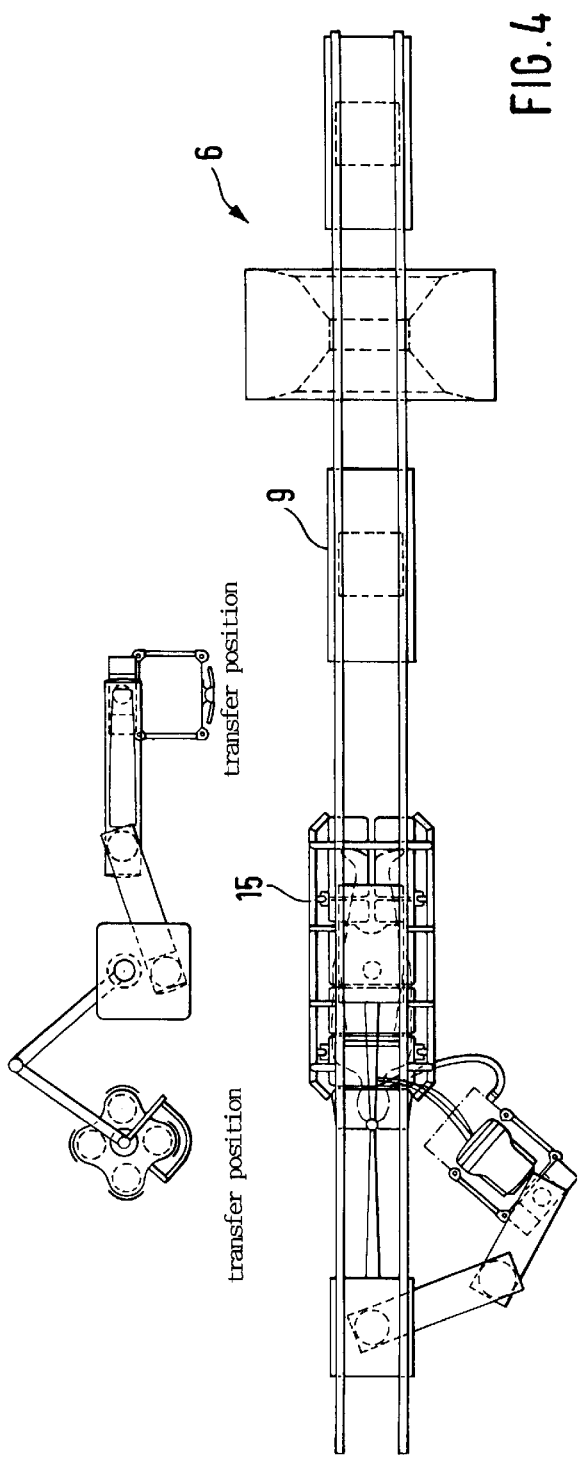

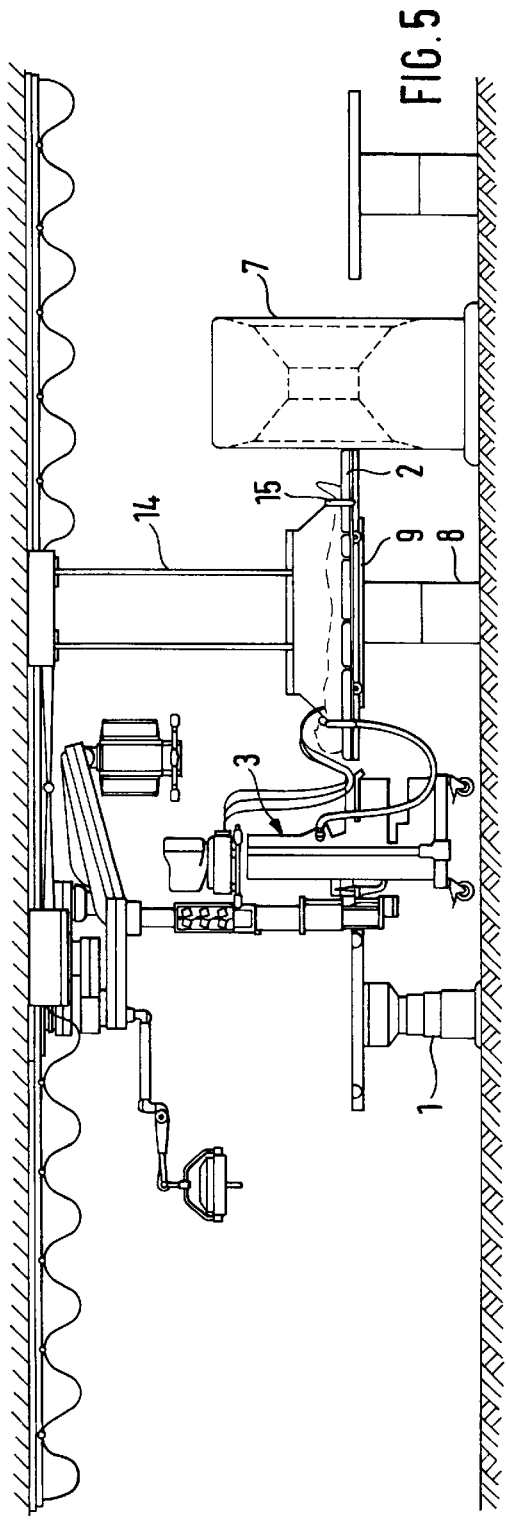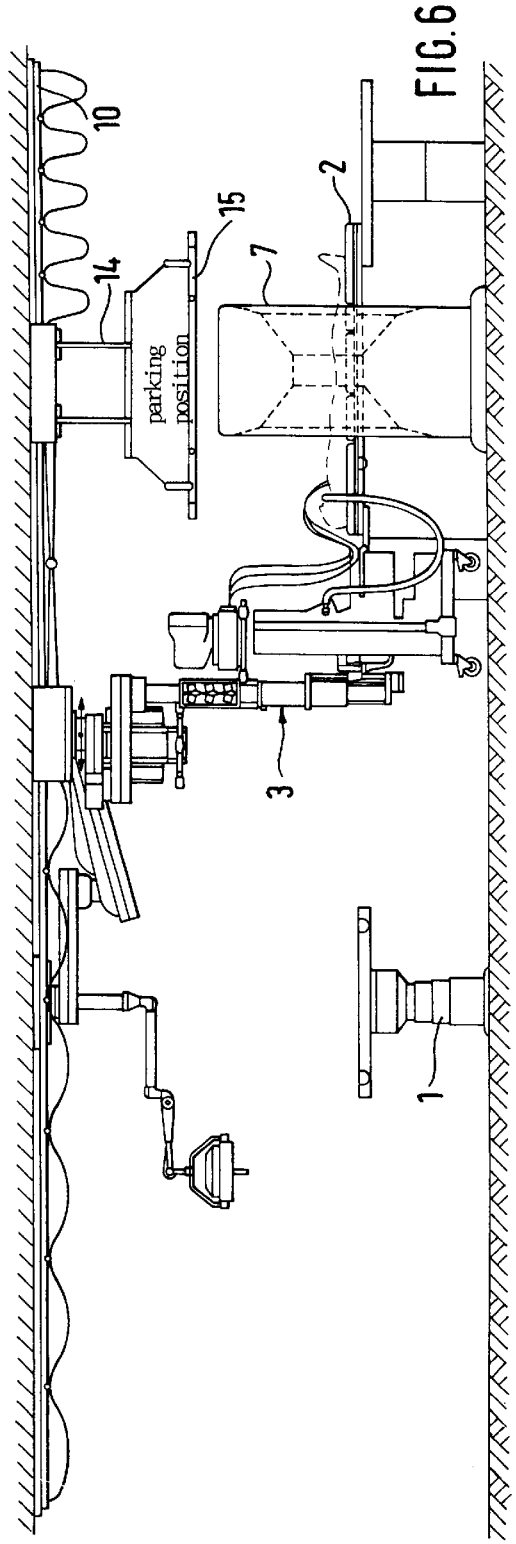

OPERATING APPARATUS COMPRISING AN OPERATING SUPPORT POST WITH A DETACHABLE OPERATING TABLE TOP

BACKGROUND OF THE INVENTION

The invention relates to an operating apparatus comprising an operating table with an operating support post and a detachable operating table top, an anesthesis station and an examining station located at a distance from the operating table.

With seriously injured persons any transfer for transport between various stations is a considerable risk. In order to reduce this risk a transportable operating table top was designed and structurally adapted to be used also as a bed for the patient to be examined in an examining station.

OBJECTS OF THE INVENTION

It is an object of the invention to provide an improved operating apparatus. It is a further object of the invention to provide an operating apparatus whereby the patient's care is further improved. It is a still further object of the invention to provide an operating apparatus which enhances the safety for the patient and the user.

SUMMARY OF THE INVENTION

According to the invention an operating apparatus comprises an operating table with an operating support post, an operating table top and means for detachably fastening said operating table top to said operating support post, an anesthesis station, an examining station located at a distance from the operating support post and comprising an examining support post for receiving the operating table top, an overhead rail extending above the operating table and the examining station, an overhead conveyor comprising means for carrying the operating table top, the overhead conveyor being mounted on the overhead rail for movement therealong between a first position above the operating support post and a second position above the examining station, an overhead support carrying said anesthesis station and being mounted on the overhead rail for movement therealong, first coupling means provided on the overhead conveyor and second coupling means provided on the overhead support, the first coupling means engaging the second coupling means in the first position of the overhead conveyor.

BRIEF DESCRIPTION OF THE DRAWINGS

Further advantages, features and objects of the invention will be apparent from the following description of an exemplary embodiment with reference to the drawings. In the drawings FIG. 1 is a side view of the operation apparatus in operating position;

FIG. 2 is a top view of the operating apparatus shown in FIG. 1;

FIG. 3 is a side view of the operating apparatus in a position for receiving the operating table;

FIG. 4 is a top view of the apparatus shown in FIG. 3;

FIG. 5 is a side view of the operating apparatus in depositing position; and

FIG. 6 is a side view of the operating apparatus in examining position.

DESCRIPTION OF A PREFERRED EMBODIMENT

As best shown in FIGS. 1 and 2 the operating apparatus comprises an operating table with an operating table post 1 having a retainer frame and an operating table top 2 detachably mounted thereon. An anesthesis station 3 with the usual devices such as monitor, anesthesis device and infusion system is provided at the head side of the operating table. The devices of the anesthesis station 3 are integrally provided at a post 4 and carried by an arm of an overhead support 5.

A tomography station 6 is disposed at the side of the operating table opposite to the head side and at a distance therefrom. The tomography station comprises a tomograph 7, a support post 8 at the inlet side of the tomograph 7 facing the operating table and a support post 8.1 on the opposite outlet side of the tomograph. Both support posts 8, 8.1 are provided with corresponding support frames 9 for receiving the operating table top 2.

A rail 10 formed as a pair of rails is provided at the ceiling of the operating theatre. The rail may also be formed as a single rail. As best shown in FIG. 2 a surgery station 11 including a pivotable operating light 12 and a support head 13 supporting surgery devices and auxiliary equipment is disposed laterally of the operating table and of the rail.

As best shown in FIG. 1 an overhead conveyor 14 for the operating table is provided at the rail 10 between the overhead support 5 and the tomography station 6. The overhead conveyor comprises a carriage 18 and a retainer frame 15 which is vertically movable in direction of the arrow 16 and rotatably supported, as indicated by the arrow 17. A first coupling member 19 is arranged at the carriage 18 to extend towards the overhead support 5. The overhead support 5 comprises a second carriage 20 corresponding to the carriage of the overhead conveyor. The second carriage is provided with a second coupling member 21 facing the first coupling member 19 and adapted to engage the first coupling member 19.

As best shown in FIGS. 3 and 4 the overhead conveyor 14 is movable in direction towards the support post 1 to receive the operating table top 2. As further shown in particular in FIG. 3 the first and second coupling members 19, 21 are connected with the carriage 18 and the second carriage 20, resp., through corresponding arms 22, 23. The length of the arms 22, 23 is selected so that the first and second coupling members come into mutual engagement in the position shown in FIG. 3, if the overhead conveyor 14 is in a position receiving the operating table top 2. This position is determined by a control cam which is adjustably mounted at the rail 10 and triggers via limit switches an electromagnetic brake built into the carriage 18. The connection of the coupling members also prevents any movement of the anesthesis station away from the patient which excludes any separation of the tubes and cables, i.e. mortal danger.

The overhead conveyor 14 is adapted so that the retainer frame 15 can be manually connected with the operating table top 2 for receiving the latter. The overhead conveyor 14 comprises a motor drive for vertical adjustment of the retainer frame 15. This drive is controlled by a sensor detecting whether the first and second coupling member 19, 21 are connected or not. The control of the motor drive is adapted to change the elevation of the retainer frame 15 only in case it is determined that both coupling members 19, 21 are engaged and connected.

As shown in the figures the overhead conveyor 14 can be moved back and forth between the receiving/depositing position shown in FIG. 3 for receiving/depositing the operating table top 2 from/on the operating table to a depositing/receiving position above the support post 8 shown in FIG. 5 and to a third parking position shown in FIG. 6. The operating table top 2 can be moved back and forth between the operating table position shown in FIG. 1 and the tomography post position shown in FIG. 5 by means of the overhead conveyor 14 and the retainer frame 15. The movement may be effected, as desired, either by hand or by an electric motor incorporated in the carriage 18 of the overhead conveyor 14. The above-described forced connection forces the operating table top to be always displaced together with the anesthesis station 3 coupled thereto for care of the patient. In the position shown in FIG. 5 the movement is stopped by a second control cam mounted to the rail 10; in manual operation the electromagnetic brake alone is switched on, in motor operation the motor is switched off and the magnetic brake is switched on, simultaneously with releasing the downward movement of the retainer frame which is manually started. After depositing the operating table top 2 on the support frame 9 and connection thereto the upward movement of the retainer frame 15 is released and again manually started. After attaining the elevational position shown in FIG. 6 which excludes collision between the retainer frame 15 and the tomograph 7 sensors release the examination which is started from outside of the room because of the radiation hazard. After starting examination the operating table top 2 with the patient lying thereon is moved in conventional manner into the aperture of the tomograph 7. In order to maintain the position of the hoses and cables between the patient and the anesthesis station, as defined in the beginning of the anesthesis, the motor driven overhead conveyor 14 pulls the anesthesis station 3 together and synchronously with the operating table top 2 into the position shown in FIG. 6. In this position a third control cam mounted at the rail 10 switches the motor off and safely stops the carriage 18 by means of the electromagnetic brake. After examination the movement is reversed whereby the first coupling member 19 can not be decoupled from the second coupling member 21 before attaining the receiving/depositing position shown in FIG. 3.

In the above embodiment the apparatus is described for transport of the operating table top 2 together with an anesthesis station between the operating table and a tomograph. The same apparatus may be used for transport between the operating table and any other working or examining station in an operating theatre.

Although the invention has been described with reference to a specific example embodiment, it is to be understood that it is intended to cover all modifications and equivalents within the spirit and scope of the appended claims.

What is claimed is:

1. An operating apparatus comprising an operating table with an operating support post, an operating table top and means for detachably fastening said operating table top to said operating support post,
   an anesthesis station,
   an examining station located at a distance from said operating table and comprising an examining support post for receiving said operating table top,
   an overhead rail extending above said operating table and said examining station,
   an overhead conveyor comprising means for carrying said operating table top, said overhead conveyor being mounted on said overhead rail for movement thereal-ong between a first position above said operating support post and a second position above said examining station,
   an overhead support carrying said anesthesis station and being mounted on said overhead rail for movement therealong,
   first coupling means provided on said overhead conveyor,
   second coupling means provided on said overhead support,
   said first coupling means engaging said second coupling means in said first position of said overhead conveyor.

2. The operating apparatus of claim 1, wherein said overhead support is movable along said overhead rail, together with said overhead conveyor with said first coupling means being coupled to said second coupling means, to said second position for depositing said operating table top on said examining support post.

3. The operating apparatus of claim 1, said overhead rail being extended beyond said examining station to permit movement of said overhead conveyor together with said overhead support coupled thereto to a third position synchronous with the movement of the operating table top.

4. The operating apparatus of claim 3, comprising stop means for stopping movement of said overhead conveyor with the anesthesis station coupled thereto in said third position.

5. The operating apparatus of claim 3, comprising means for locking the position of said anesthesis station in said third position.

6. The operating apparatus of claim 3, comprising means for enabling movement between said second and third position only if a retainer frame coupled to said overhead conveyor for carrying said operating table top is at an elevation higher than said examining station.

7. The operating apparatus of claim 1, comprising a retainer frame provided at said overhead conveyor for receiving said operating table top, and means for releasing vertical movement of said retainer frame only, if said overhead conveyor is in a first position.

8. The operating apparatus of claim 1, wherein said examining station comprises a tomograph.

9. The operating apparatus of claim 1, wherein said examining station is replaced by a radiation therapy device (linear accelerator) positioned within the same operating theatre as said operating table.

10. An operating apparatus comprising an operating table with an operating table top, a carrier cloth on said operating table top for carrying a patient thereon and a retainer frame for carrying said carrier cloth with a patient thereon,
    an anesthesis station,
    an examining station located at a distance from said operating table and comprising an examining table for receiving said carrier cloth with the patient thereon,
    an overhead rail extending above said operating table and said examining station,
    an overhead conveyor comprising means for attachment to said retainer frame for carrying said carrier cloth, said overhead conveyor being mounted on said overhead rail for movement therealong between a first position above said operating table and a second position above said examining station,
    an overhead support carrying said anesthesis station and being mounted on said overhead rail for movement therealong,
    first coupling means provided on said overhead conveyor and second coupling means provided on said overhead support, said first coupling means engaging said second coupling means in said first position of said overhead conveyor.

11. The operating apparatus of claim 10, comprising means for moving said overhead conveyor, with the retainer frame retaining said carrier cloth attached thereto and said overhead support coupled thereto by engagement of said first coupling means with said second coupling means, from said first position to said second position, and means for depositing said carrier cloth on a table provided in said examining station.

* * * * *